United States Patent [19]

Braverman

[11] Patent Number: 5,163,444
[45] Date of Patent: Nov. 17, 1992

[54] METHOD FOR INCREASING THE AMPLITUDE OF P300 WAVES IN THE HUMAN BRAIN

[76] Inventor: Eric Braverman, 844 Rte. 518, Skillman, N.J. 08558

[21] Appl. No.: 593,067

[22] Filed: Oct. 5, 1990

[51] Int. Cl.⁵ .............................................. A61N 1/36
[52] U.S. Cl. ................................ 128/783; 128/419 R; 128/420 R; 128/421; 128/898
[58] Field of Search ............ 128/419 B, 419 C, 419 S, 128/420 A, 420 R, 420.5, 421, 422, 731, 732, 741, 898, 791, 796, 802, 783, 419 R; 606/32, 34; 600/26

[56] References Cited

U.S. PATENT DOCUMENTS

| | | | |
|---|---|---|---|
| 238,721 | 3/1881 | Sharp | 128/377 |
| 3,718,132 | 2/1973 | Holt et al. | 600/26 |
| 4,014,323 | 3/1977 | Gilmer et al. | 128/422 |
| 4,719,922 | 1/1988 | Padjen et al. | 128/421 |
| 4,782,837 | 11/1988 | Hogan | 128/421 |
| 4,785,813 | 11/1988 | Petrofsky | 128/421 |
| 4,865,048 | 9/1989 | Eckerson | 128/791 |

FOREIGN PATENT DOCUMENTS

8700063  1/1987  World Int. Prop. O.

OTHER PUBLICATIONS

Silverman et al., IEEE Transactions on Biomedical Engineering, vol. BME-22, No. 3, pp. 207-212, May 1975.
Neuro Systems Inc., "The RelaxPak" Sales brochure, 1986.
"Electrosleep", R. L. Williams, pp. 39-41, Jan. 13, 1966.
Davis, Gibbs, Davis, Jetter and Trowbridge, *The Effects of Alcohol upon the Electroencephalogram (Brain Waves)*, pp. 626-637.
Funkhouser, Nagler and Walke, *The Electro-Encephalogram of Chronic Alcoholism*, Southern Medical Journal, vol. 46, No. 5, pp. 423-428 (May 1953).
Little and McAvoy, *Electroencephalographic Studies in Alcoholism*, pp. 9-15.
Pfefferbaum, Horvath, Both and Kopell, *Event-Related Potential Changes in Chronic Alcoholics*, Electroencephalography and Clinical Neurophysiology, vol. 47, pp. 637-647 (1979).
Propping, *Genetic Control of Ethanol Action on the Central Servous System*, Human Genetics, vol. 35, pp. 309-334 (1977).
Gabrielli, Mednick, Volavka, Pollock, Schulsinger and Turan *Electroencephalograms in Children of Alcoholic Fathers*, Psychophysiology, vol. 19, No. 4 (Jul. 1982).
Begleiter and Porjesz, *Neuroelectric Processes in Individual Risk for Alcoholism*, Alcohol & Alcoholism, vol. 25, No. 2/3, pp. 251-256 (1990).
Whipple, Parker & Noble, *An Atypical Neurogognitive Profile in Alcoholic Fathers and Their Sons*, Journal of Studies on Alcohol, vol. 49, No. 3 pp. 240-244 (May 1988).
Polich, Burns & Bloom, *P300 and the Risk of Alcoholism: Family History, Task Difficulty, and Gender*, Alcoholism Clinical and Experimental Research, vol. 12, No. 2 (Mar.-Apr. 1989).
Polich, Volavka, Goodwin, Mednick, Gabrielli, Knop and Schulsinger, *The EEG after Alcohol Administration in mean at Risk for Alcoholism*, Arch Gen Psychiatry, vol. 40, pp. 857-861 (Aug. 1983).
Volavka, Pollock, Gabrielli and Mednick, *The EEG in Persons at Risk for Alcoholism*, High Risk Studies of Alcoholism, pp. 21-35.
Schuckit, Gold, Croot, Finn & Polich, *P300 Latency after Ethanol Ingestion in Sons of Alcoholics and in Controls*, Biol. Psychiatry, 24:310-315 (1988).
O'Connor, Hesselbrook, Tasman & DePalma, *P300 Amplitudes in Two Distinct Tasks are Decreased in Young Men with A History of Paternal Alcoholism*, Alcohol, vol. 4, pp. 323-300 (1987).
O'Connor and Tasman, *The Application of Electrophysiology to Research in Alcoholism*, Journal of Neuropsychiatry, vol. 2, No. 2, pp. 149-168 (Spring 1990).
Dawood and Ramos, *Transcutaneous Electrical Nerve Stimulation (TENS) for the Treatment of Primary Dysmenorrha: A Randomized Crossover Comparison with Placebo TENS and Ibuprofen*.
Smith, *Neural Stimulation*, Chapter 15, Cranial Electrotherapy Stimulation, CRC Press, Inc.
Kotter, Kenschel, Hogan and Kalbfleisch, *Inhibition of Gastric Acid Secretion in Man by the Transcranial Appli-* cation of Law Intensity Pulsed Current, Gastroenterology, vol. 69, No. 2, pp. 359-362 (1975).

Schmitt, Capo, Frazier and Boren, *Cranial Electrotherapy Stimulation Treatment of Cognitive Brain Dysfunction in Chemical Dependence,* Journal of Clinical Psychiatry, vol. 45, No. 2, (Feb. 1984).

Smith, *Confirming Evidence of an Effective Treatment for Brain Dysfunction in Alcoholic Patients,* The Journal of Nervous and Mental Diseases, vol. 170, No. 5, pp. 275-277 (1985).

Smith & Day, *The Effects of Cerebral Electrotherapy on Short-Term Memory Impairment in Alcoholic Patients,* The International Journal of the Addictions, vol. 12, No. 4, pp. 575-582 (1977).

Jarzembski, *Electrical Stimulation and Substance Abuse Treatment,* Neurobehavioral Toxicology and Teratology, vol. 7, pp. 119-123 (1985).

Wilson and Childs, *CES Cranial Electrotherapy Stimulation, Cranial Electrotherapy Stimulation for Attention-to-Task Deficit: A Case Study,* American Journal of Electromedicine, pp. 93-99 (Dec. 1988).

Grinenko, Krupitskiy, Lebedev, Katsnelson, Karandashova, Moshkov, Buljon, Illiukchina and Borodkin, *Metabolism of Biogenic Amines during the Treatment of Alcohol Withdrawal Syndrome by Transcranial Electric Treatment,* Biogenci Amines, vol. 5, No. 6, pp. 426-427 (1988).

CES Labs—CES 100 Hz User's Manual.
Healthpax Sales Brochures.
Medi Consultants, Inc. Sales Brochure.

List of references relating to Transcutaneous Electrical Nerve Stimulation Applications.

*Primary Examiner*—David M. Shay
*Attorney, Agent, or Firm*—Mathews, Woodbridge & Collins

[57] ABSTRACT

A cranial electrotherapy stimulation ("CES") device which generates electrical pulses is applied between the forehead and wrist area of a human being in order to affect electrical activity in the brain and thereby decrease the individual's craving for controlled substances such as alcohol and drugs and reduce anxiety, insomnia and depression. A portable cranial electrical stimulator is preferably attached to the arm area or about the waist of a patient. A first electrode is attached to the forehead of the patient, preferably above the bridge of the nose between the eyes, and a second electrode is attached to the wrist area of one arm, preferably at the radial artery. Electrical pulses having an amplitude in the range of 0.1 to 1.5 mA and a frequency of approximately 100 Hz are applied for at least 20 minutes at a 20% duty cycle between the forehead and the wrist electrodes. As a result, electrical activity in the brain is affected, in particular, the amplitude of P300 electrical brain activity is increased. Since decreased P300 activity is associated with increased patient interest in drugs and alcohol, the use of the CES in this way makes it less likely that the patient will desire such controlled substances.

5 Claims, 3 Drawing Sheets

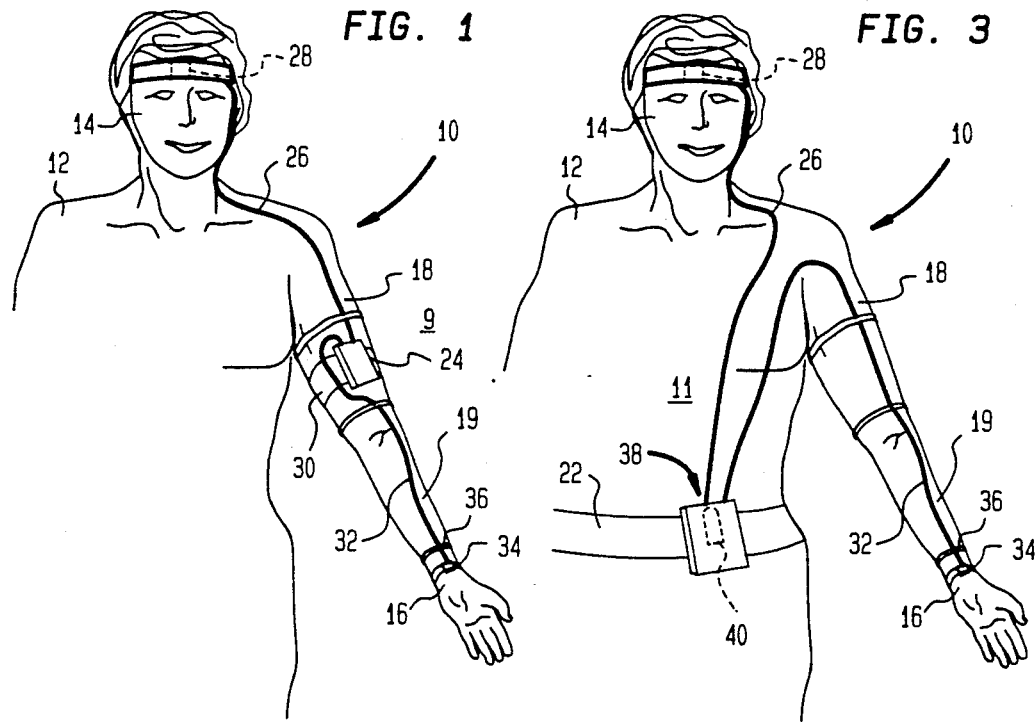
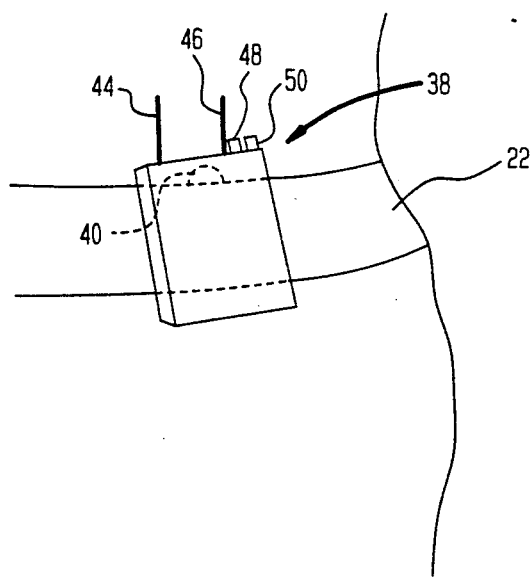
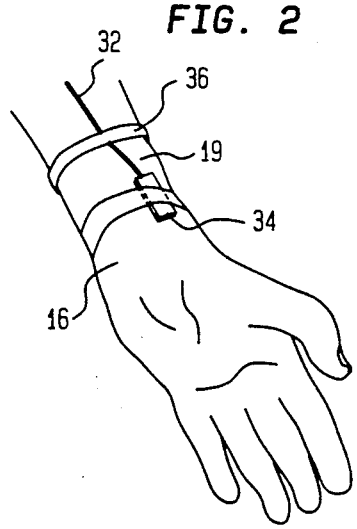

METHOD FOR INCREASING THE AMPLITUDE OF P300 WAVES IN THE HUMAN BRAIN

BACKGROUND OF INVENTION

1. Field of the Invention

The invention relates to a method and apparatus for increasing electrical brain activity, in particular the amplitude of P300 waves, thereby decreasing cravings for addictive substances by providing cranial electrical stimulation between the forehead and wrist area of a patient.

2. Description of the Related Art

P300 waves are electrical waves which occur in the human brain. They are a cognitive evoked potential in response to a stimulus to the brain known as an "oddball paradigm of beeps". The P300 wave occurs at approximately 300 ms from the initial stimulation of a patient with the oddball paradigm and are measured using a quantified EEG machine such as a device known as a BEAM ("Brain Electrical Activity Map"). The "P" stands for "Positive". Various researchers have correlated a diminished activity of P300 waves with an increase in craving for alcohol and other addictive drugs. See e.g., Begleiter & Projesz, *Neuroele Processes in Individuals at Risk for Alcoholism,* Alcohol & Alcoholism, Vol, 25:251–256 (1990); Begleiter, Projesz, *Rawlinos & Echardt, Auditory Recovery Function and P3 in Boys at High Risk for Alcoholism,* Alcohol, Vol. 4:315–321 (1987); Begleiter & Projesz, *The P300 Component of the Event-Related Brain Potential in Psychiatric Patients,* Evoked Potential, 529–535, New York: Alan R. Liss, Inc. (1986); Whipple, Parker & Noble, *An Atypical Neurocognitive Profile in Alcoholic Fathers and Their Sons,* Journal of Studies on Alcohol, Vol. 43:240–244 (1988); Polich, Burns, & Bloom, *P300 and the Risk for Alcoholism.* Clinical and Experimental Research, Vol. 12:248–254 (1988); Schukits, Gold, Croot, Finn & Polich, *P300 Latency After Ethanol Inoestion in Sons of Alcoholics and in Controls.* Biological Psychiatry, Vol. 24:310–315 (1988); O'Connor, Hesselbroch, Tasman, Depalma, *P3 Amplitudes in Two Distinct Tasks are Decreased in Young Men with a History of Paternal Alcoholism,* Alcohol Vol. 4:323–330 (1987). The amplitude of P300 waves is a measure of concentration, attention and anxiety. An increase in P300 wave amplitude probably has applications beyond a decrease in cravings for alcohol and drugs (i.e., reduction of anxiety, depression and insomnia).

Cranial Electrotherapy Stimulation ("CES") is a term applied by the U.S. Food and Drug Administration ("FDA") to the transcranial application of small amounts of electricity, usually less than 1.5 mA at 100 Hz, to the head of a human being. It was originally used in the 1960's to induce sleep.

Prior art applications of CES devices have involved the use of higher frequencies, e.g., Liss, whose device operates at 15 kHz, the electrodes being attached to the head at the temples by means of a headband device. Researchers have shown that CES at 100 Hz is beneficial to alcoholics and drug abusers when attached to the mastoids. See, e.g., Smith, *Cranial Electrotherapy Stimulation, Neural Stimulation,* Vol. II: 129–150, Boca Raton, Fla., CRC Press Inc. (1985); Schmitt, *Capo. Frazier & Cranial Electrotherapy Stimulation Treatment of Cognitive Brain Dysfunction in Chemical Dependence,* Journal of Clinical Psychiatry, Vol. 45:60–63 (1984); Smith, *Confirming Evidence of an Effective Treatment of Brain Dysfunction in Alcoholic Patients,* Journal of Nervous and Mental Disease, Vol. 170:275–78 (1982) and Smith & Day, *The Effects of Cerebral Electrotherapy on Short-Term Memory Impairment in Alcoholic Patients.* International Journal of the Addictions, Vol. 12(4):574–82 (1977). However, the placement of the electrodes on the wrist and forehead, as disclosed herein, as opposed to the mastoids has greater beneficial effects on brain waves, in particular, increasing P300 wave amplitude in alcoholics and drug abusers. Both positions tend to normalize brain waves, but the placement of the electrodes on the forehead and wrist has the added beneficial effect on P300 wave amplitude.

The FDA has approved numerous CES devices for the treatment of anxiety, insomnia and depression. Several thousand patients are treated using CES devices annually in America. Existing CES devices are used by connecting electrodes to patients' mastoids, earlobes or temples. There have been anecdotal reports of studies using the CES device on the leg and the head. There have also been studies in which the electrodes have been connected to the temples, forehead, and eyelids, but not simultaneously to the wrist and the forehead. The connection of a CES device between the forehead and the wrist, stimulating the patient with a square wave at 100 Hz and a maximum of 1.5 mA to increase P300 wave activity does not appear to be taught or suggested by the prior art.

SUMMARY OF THE INVENTION

Briefly described the invention comprises a cranial electrotherapy stimulation ("CES") device which generates a square current waveform of frequency 100 Hz, amplitude in the range of 0.1 to 1.5 mA, voltage of approximately 50 v and 20% duty cycle. The CES device has two outputs, one of which is connected to the forehead and the other of which is connected to the wrist of a patient. The patient is stimulated with the device for between 20 minutes and two hours. Such stimulation results in an increase in the amplitude of P300 waves in the brain which in turn is associated with a decrease in cravings for alcohol and drugs.

The invention may be more fully understood by reference to the following drawings.

BRIEF DESCRIPTION OF THE DRAWINGS

FIG. 1 is a view of a person using the preferred embodiment of the invention with the CES device carried on the bicep.

FIG. 2 is a detail showing the wrist electrode connected to the person's wrist at the radial artery.

FIG. 3 is a view of an alternative embodiment of the invention in which the CES device is worn on a belt around the waist.

FIG. 4 shows the CES device attached to the waist of the person by means of a belt.

DETAILED DESCRIPTION OF THE PREFERRED EMBODIMENT

Figure 5:
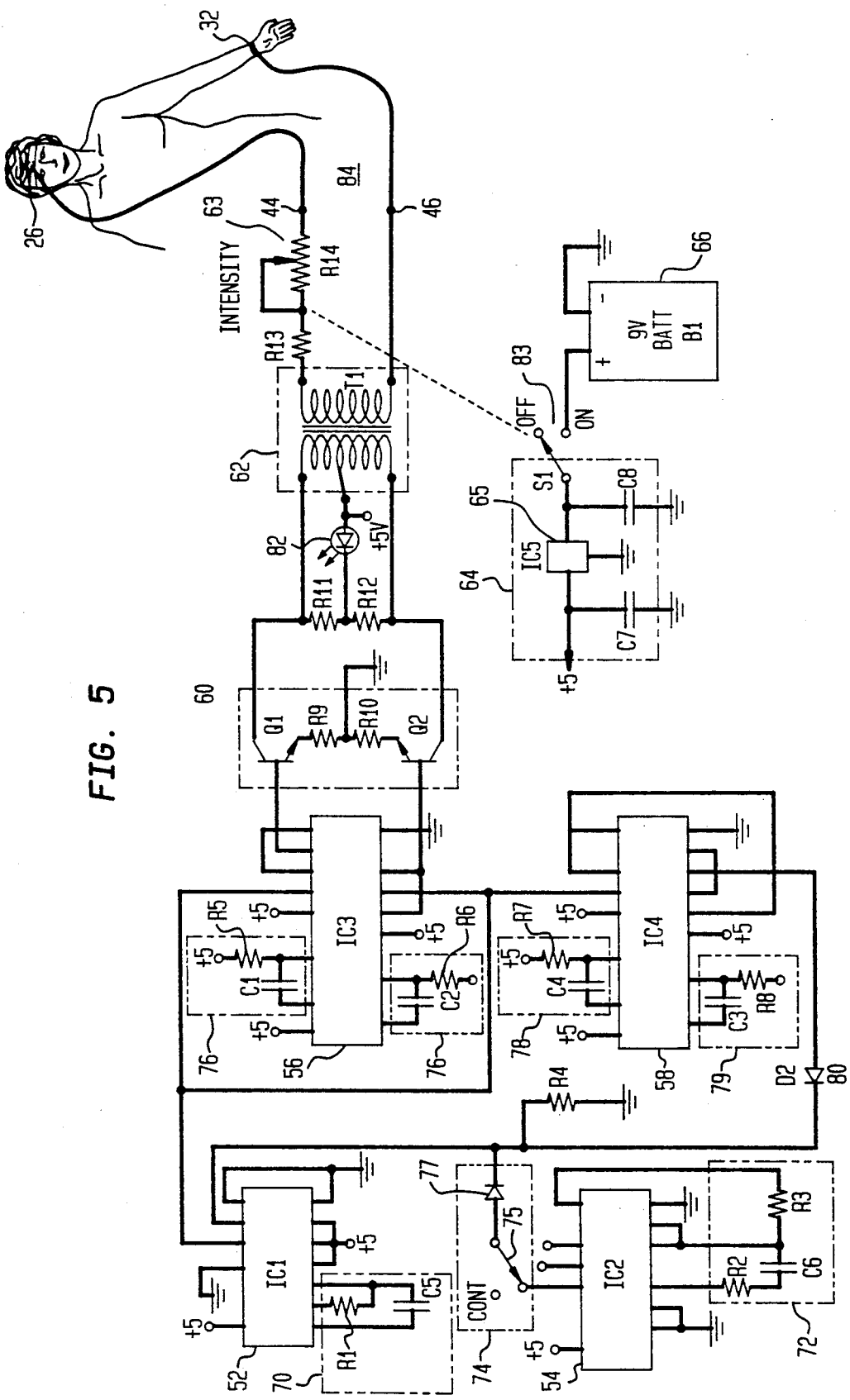
FIG. 5 is a schematic diagram of the electrical circuitry of the CES.

During the course of this description like numbers will be used to indicate like elements according to the different views of the invention.

FIG. 1 illustrates the preferred embodiment 9 of invention 10. A CES device 24 is shown attached to the arm 18 of patient 10 by means of strap 30. In FIG. 3, which illustrates an alternative embodiment 11 of invention 10, the CES device 38 is attached to the waist of patient 10 by means of clip 40 and belt 22.

FIG. 4 illustrates the CES device 38 attached to the waist of patient 10 as in the alternative embodiment 11. FIG. 4 also illustrates the output ports 44 and 46 of CES device 38, switch 48, which is used to turn the CES device on and off, and control knob 50, which is used to adjust the output of the device 8. Output ports 44 and 46, switch 48 and control knob 50 are present (but not shown) in both embodiments 9 and 11.

An example of an acceptable portable CES device 24 or 38 is the unit marketed under the name "Healthpax" by Health Directories Inc. of 411 W. Trenton Avenue, Morrisville, Pa. 19067. Similar devices are manufactured by various other companies such as CES Labs, 14770 N.E. 95th Street, Redmond, Wash. 98052, Neuro-Systems, Inc., 11235 Pegasus, Suite E-102, Dallas, Tex. 75238 and Neurotek, Inc., 750 East Campbell Road, Suite 600, Richardson, Tex. 75081.

In both embodiments 9 and 11, the head electrode 28 is attached to the patient's head 14, preferably at a point immediately above the bridge of the nose and between the eyes. A wrist electrode 34 is attached to the wrist 16 of the patient, preferably at the radial artery. The wrist electrode preferably acts as an electrical ground point. The head electrode 28 and the wrist electrode 34 are respectively connected to the output ports 44 and 46 of the CES device 38 or 24 (depending on the embodiment) by means of head electrode wire 26 and wrist electrode wire 32.

The head electrode 28 and the wrist electrode 34 are conventional medical gel electrodes such as those available from Transcutek of 13100 So. 300 East Draper, Utah 84020 or Mr. Electrode, Beck Lee Co., P.O. Box 425, Stratford, Conn. 06497. Alternatively, the head electrode 28 may be a copper conducting wire, held in place by means of a headband fastened by Velcro ® strips or an elastic material. The wrist electrode 34 may also be a copper conducting wire, held in place by a wrist band secured by Velcro ® strips or an elastic material.

Once the head electrode 28 and wrist electrode 34 are in place, the CES device is switched by means of switch 48 on CES device 38 or 24. The output current of the CES device is adjusted to between 0.1 and 1.5 mA using the control knob 50 on the CES device. The output current level is selected depending on the patient's comfort level. The highest level tolerable to the patient is preferable. The patient is stimulated in this way for between 20 minutes and two hours. After approximately 20 minutes there are likely to be significant changes in the activity of various electrical waves in the patient's brain. In particular, the amplitude of P300 waves is likely to increase significantly after approximately 40 minutes of stimulation in this way. Further applications of stimulation over a period of weeks have an increased beneficial effect.

FIG. 5 is an electrical schematic diagram of the portable, internal electrical circuit of the preferred embodiment of CES device 28 or 34. The components of the circuit are mounted on an appropriately laid out printed circuit board.

Integrated circuit 52 is an astable multivibrator producing a square wave output between 0 and 5 volts, available from Harris Semiconductor, Inc., Part No. CD4047B. Resistor-capacitor combination 70 determines the frequency of the output of integrated circuit 52. Integrated Circuit 54 is an electronic counter with a built in oscillator to produce time delays to control the amplitude of the output waveform of the CES device 28 or 34. Integrated circuit 54 is available from Harris Semiconductor, Inc., Part No. CD4521B. Resistor-capacitor combination 72 controls the time of application of the output waveform. Integrated circuit 54 is controlled by timer 74. Timer 74 includes a switch 75, which is a standard single pole four position switch available from Mouser Electronics, and diode 77 which is a germanium low forward drop diode available from National Semiconductor Corp., Part No. IN4305. Integrated circuit 56 is a dual one shot circuit consisting of two single pulse generators to generate output pulses. Integrated circuit 56 produces a series of two positive pulses followed by two negative pulses. Integrated circuit 56 is available from Harris Semiconductor, Inc., Part No. CD4538B. Resistor capacitor combination 76 controls the pulse width and time delay of the output pulses. Integrated circuit 58 is a second dual one shot circuit and is identical to integrated circuit 56. Integrated circuit 58 controls the time that the output pulses are on or off and produces the 20% duty cycle. Resistor-capacitor combinations 78 and 79 control the pulse width and time delay. Transistor-resistor combination 60 amplifies the output current of integrated circuit 56 in order to drive transformer 62. The transistors used in transistor-resistor combination 60 are standard NPN transistors available from Motorola Inc., Part No 2N2222. Transformer 63 is an open frame transformer available from Mouser Electronics, Part No. 422TM002. Transformer 62 isolates the output and steps up the voltage to 40 volts peak (80 volts peak to peak). Potentiometer 62 is a standard 50K potentiometer which controls the current output intensity. Voltage regulator 64 comprises a voltage regulator integrated circuit 65 which produces a regulated output of 5 volts, available from Linear Technology Corp., Part No. LM2931Z5. Battery 66 is a standard 9 volt alkaline battery. Diode 80 is a germanium low forward drop diode available from National Semiconductor Corp., Part No. 1N4305. Light emitting diode 82 is a standard light emitting diode available from Mouser Electronics, Part No. F350001. Light emitting diode 82 is lit when the device is switched on by means of on/off switch 83.

The output 84 comprises two standard electrical pin-jacks to which output ports 44 and 46 are connected.

The values of the various resistors and capacitors are as follows:

| | | |
|---|---|---|
| $R_1 = 10\ K\Omega$ | $R_{10} = 47\ K\Omega$ | $C_5 = 0.1\ \mu F$ |
| $R_2 = 1\ M\Omega$ | $R_{11} = 1\ K\Omega$ | $C_6 = 0.1\ \mu F$ |
| $R_3 = 75\ K\Omega$ | $R_{12} = 1\ K\Omega$ | $C_7 = 0.1\ \mu F$ |
| $R_4 = 100\ K\Omega$ | $R_{13} = 4.3\ K\Omega$ | $C_8 = 0.1\ \mu F$ |
| $R_5 = 47\ K\Omega$ | $R_{14} = 50\ k\Omega$ | |
| $R_6 = 47\ K\Omega$ | $C_1 = 0.1\ \mu F$ | |

| -continued | |
|---|---|
| $R_7 = 36\ K\Omega$ | $C_2 = 0.1\ \mu F$ |
| $R_8 = 150\ \Omega$ | $C_3 = 0.1\ \mu F$ |
| $R_9 = 47\ \Omega$ | $C_4 = 0.1\ \mu F$ |

The power rating for all resistors is ⅛ W. The voltage rating for all capacitors is 20 V minimum.

Figure 6:
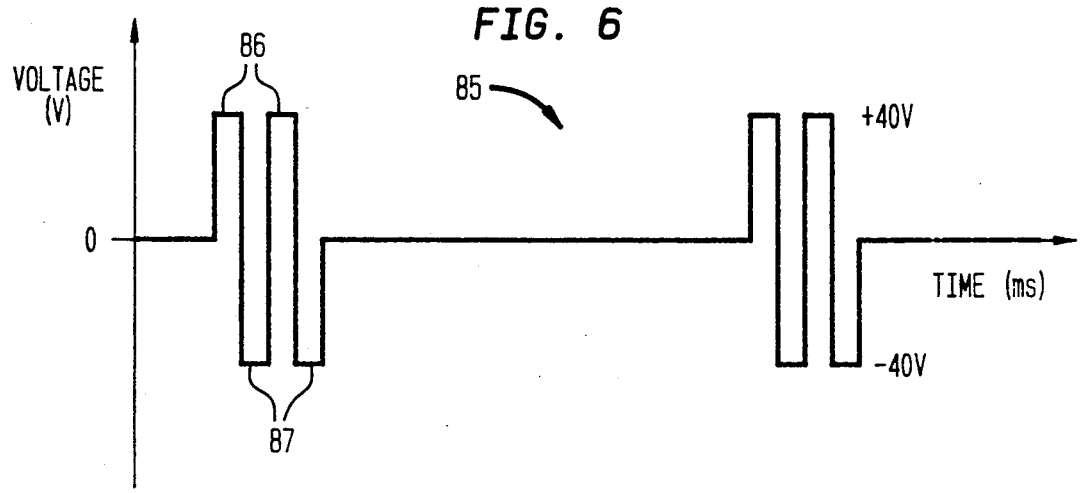
FIG. 6 is a graph of a preferred waveform output of the CES device.

FIG. 6 shows the preferred current waveform output 85 of the CES device at the output 84 under no-load conditions. A single cycle of the current waveform 85 has a period of 12.2 ms. A single cycle consists of two peaks 86 of amplitude 40 V, two troughs 87 of amplitude — 40 V and a rest period at 0 V of 7.8 ms. Each peak and each trough has a duration of 4.4 ms.

Experiments with patients using the invention and control experiments have yielded the following data.

In one study, 30 patients who were alcoholics or children of alcoholics, were each stimulated for 40 minutes at 100 Hz with a Healthpax CES attached to the forehead and wrist. P300 waves were measured at the central and parietal midline regions of the head. The amplitude of P300 waves as raised from 5.98±3.6 µv to 8.45±4.7 µv. These results are tabulated on Table A.

TABLE A
CHANGE IN TIME AND AMPLITUDE OF P300 WAVEFORM AT CZ AND PZ ELECTRODE IN CHILDREN OF ALCOHOLICS AND ALCOHOLICS (N = 30)

|  | PRIOR TO STIMULATION | AFTER STIMULATION |
|---|---|---|
| Time (msec) | 318.4 ± 26.0 | 329.3 ± 33.2 |
| P300 Amplitude (microvolts) | 5.98 ± 3.6 | 8.45* ± 4.7 |

*p < .0001

A further sample of 16 children of alcoholics and alcoholics were stimulated for 40 minutes at 100 Hz with Healthpax devices. P300 amplitudes increased from 4.03±3.4 µv. to 6.17±4.2 µv. These results are tabulated in Table B.

TABLE B
CHANGE IN AMPLITUDE OF P300 WAVEFORM AT FZ ELECTRODE IN CHILDREN OF ALCOHOLICS AND ALCOHOLICS (N = 16)

|  | PRIOR TO STIMULATION | AFTER STIMULATION |
|---|---|---|
| Time (msec) | 4.03 ± 3.4 | 6.17* ± 4.2 |
| P300 Amplitude (microvolts) | 314.2 ± 27.7 | 317.9 ± 28.4 |

*p < .001

After 40 minutes of stimulation with Healthpax CES's attached to the foreheads and wrists of 14 brain diseased patients, P300 waves increased from 7.0±4.1 µV to 9.9±6.1 µv. These results are tabulated on Table C.

TABLE C
MODIFICATION OF P300 WAVEFORM IN ORGANIC BRAIN DISEASED PATIENTS WEARING CES IN LEFT WRIST/CENTRAL FOREHEAD POSITION FOR 40 MINUTES (N = 14)

|  | PRIOR TO STIMULATION | AFTER STIMULATION |
|---|---|---|
| Time (msec) | 308 ± 24 | 317.1 ± 26 |
| P300 Amplitude (microvolts) | 7.0 ± 4.1 | 9.9* ± 6.1 |

*p < .03 by paired T test

Table D shows the increase in P300 wave amplitude in a sample of 29 psychiatric patients, children of alcoholics and drug abusers after application of the invention for 40 minutes. As may be seen, the amplitude of p300 waves increased from 7.05±4.4. µv to 9.18±4.5 µv.

TABLE D
MODIFICATION OF P300 IN PSYCHIATRIC PATIENTS, CHILDREN OF ALCOHOLICS AND DRUG ABUSERS AFTER 40 MINUTES OF WEARING CES IN THE WRIST/FOREHEAD POSITION (N = 29)

|  | PRIOR TO STIMULATION | AFTER STIMULATION |
|---|---|---|
| Time (msec) | 316.3 ± 23.7 | 318.2 ± 27.8 |
| Amplitude (microvolts) | 7.05 ± 3.3 | 9.18* ± 4.5 |

*p > .001 paired T test

Figure 7:
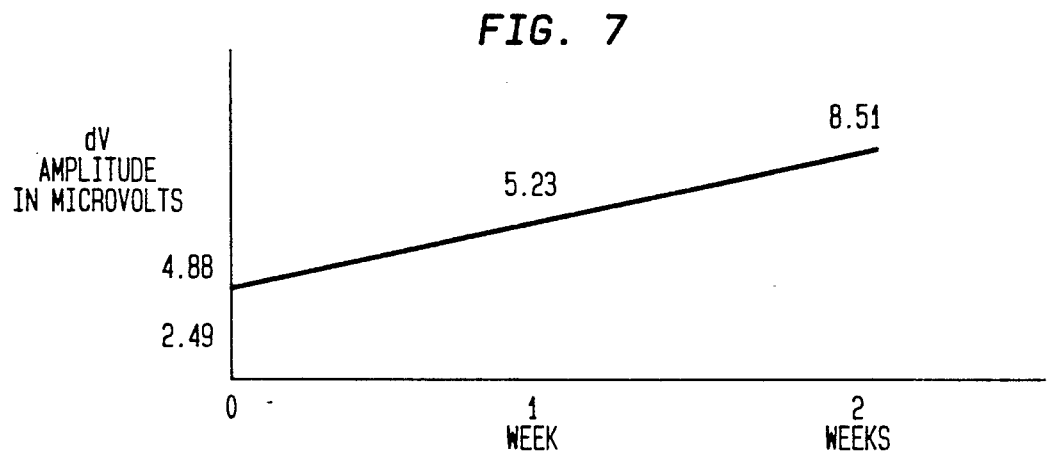
FIG. 7 is a graph showing increases in P300 wave amplitude of a 27 year old child of an alcoholic with a history of alcohol abuse after 40 minutes of stimulation using the invention over a period of two weeks.
Figure 8:
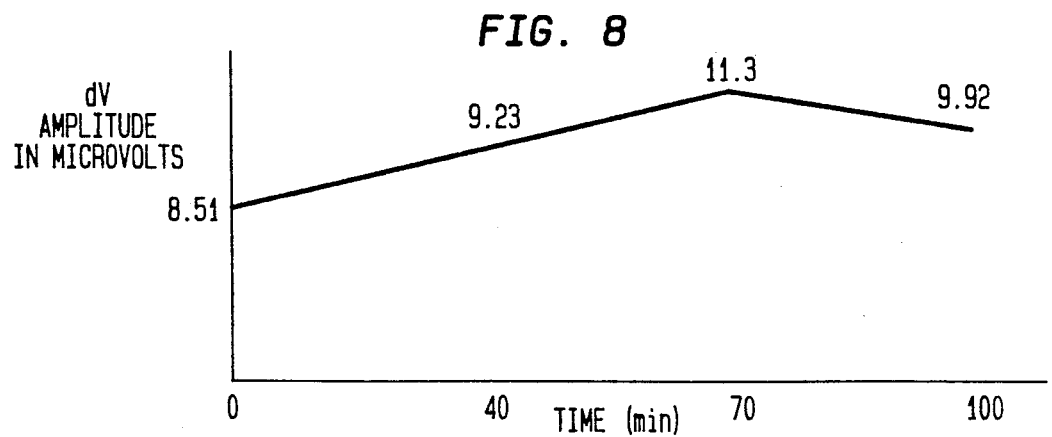
FIG. 8 is a graph showing the increase in P300 wave amplitude in a 27 year old child of an alcoholic with a history of alcohol abuse after 100 minutes of stimulation using the invention.

In one stimulated patient, the child of an alcoholic with a history of alcohol abuse, an increase in P300 amplitude from 2.49 to 8.51 µv was observed over a period of two weeks of daily treatment of such treatment for 40 minutes per day. These results are graphically represented in FIG. 7. In the same patient an increase in P300 amplitude from 8.51 to 11.3 µv was observed after a single period of 70 minutes of stimulation. These results are graphically represented in FIG. 8.

Other studies using different electrical frequencies, sham inputs and positioning the electrodes on the mastoids did not produce significant increases in P300 amplitudes.

A study involving 10 patients stimulated for 40 minutes each at 100 Hz using the Healthpax device via electrodes attached to the mastoids produced no significant change in P300 amplitude. These results are tabulated on TABLE E.

TABLE E
CHANGE IN TIME AND AMPLITUDE OF P300 WAVE FOLLOWING 40 MINUTES OF CES (HEALTH PAX) WORN ON MASTOIDS (N = 10)

|  | PRIOR TO STIMULATION | AFTER STIMULATION |
|---|---|---|
| Time (msec) | 329.2 ± 20.0 | 344.6 ± 22.2 |
| Amplitude (microvolts) | 11.2 ± 5.1 | 9.9 ± 2.3 |

A sham CES with no current output was applied to 10 patients for 40 minutes each, the electrodes being connected to the forehead and wrist. There was no significant increase in P300 amplitude in the patients. These results are tabulated on TABLE F.

TABLE F
DOCUMENTATION OF NO SIGNIFICANT CHANGE IN P300 WITH 40 MINUTES OF SHAM CES (N = 10)

|  | PRIOR TO STIMULATION | AFTER STIMULATION |
|---|---|---|
| Time (msec) | 336 ± 24 | 324 ± 27 |
| P300 Amplitude (microvolts) | 8.4 ± 3.8 | 8.4 ± 4.9 |

The foregoing results demonstrate the effectiveness of CES applied to the forehead and wrist in raising the level of P300 waves in alcoholics, children of alcoholics and brain diseased psychiatric patients.

While the invention has been described with reference to the preferred embodiment thereof, it will be appreciated by those of ordinary skill in the art that modifications can be made to the parts and steps that comprise the invention without departure from the spirit and scope of the invention as a whole.

I claim:

1. A method of increasing the amplitude of P300 waves in the brain of a human being comprising the steps of:

attaching a first electrode means to the head of said human being;

attaching a second electrode means to an arm of said human being;

applying a substantially square current waveform having a frequency of approximately 100 Hz, an amplitude of approximately 0.1 to 1.5 mA and a duty cycle of approximately 20% between said electrode means for at least 20 minutes.

2. The method of claim 1 wherein said first electrode means is attached to the forehead of said human being.

3. The method of claim 1 wherein said second electrode means is attached to a wrist of said human being.

4. The method of claim 1 further comprising the step of connecting said second electrode means to the wrist of said human being in the region of the radial artery of said wrist.

5. The method of claim 1 further comprising the step of connecting said first electrode means to the forehead of said human being between the eyes of said human being and above the bridge of the nose of said human being.

* * * * *